(12) United States Patent
Amer et al.

(10) Patent No.: US 10,481,134 B2
(45) Date of Patent: Nov. 19, 2019

(54) UNDERWATER VEHICLES WITH INTEGRATED SURFACE CLEANING AND INSPECTION

(71) Applicant: Saudi Arabian Oil Company, Dhahran (SA)

(72) Inventors: Ayman Amer, Thuwal (SA); Fadl Abdellatif, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 96 days.

(21) Appl. No.: 15/641,453

(22) Filed: Jul. 5, 2017

(65) Prior Publication Data

US 2019/0011403 A1    Jan. 10, 2019

(51) Int. Cl.
*B08B 3/02* (2006.01)
*G01N 29/24* (2006.01)
(Continued)

(52) U.S. Cl.
CPC ............. *G01N 29/245* (2013.01); *B08B 3/02* (2013.01); *B08B 9/023* (2013.01); *B08B 13/00* (2013.01);
(Continued)

(58) Field of Classification Search
CPC ....... G01N 29/245; G01N 2291/02854; G01N 17/02; G01N 29/225; G01N 29/265;
(Continued)

(56) References Cited

U.S. PATENT DOCUMENTS 3,165,899 A    1/1965    Shatto, Jr.
3,720,433 A    3/1973    Rosfelder
(Continued)

FOREIGN PATENT DOCUMENTS

EP    3163288 A2    5/2017
GB    2513560 A    11/2014

OTHER PUBLICATIONS

V-robo/30D. Suction-adhering auto traveling underwater cleaning robot. Urakami Research & Development Co., Ltd. http://www.urakami.co.jp.
(Continued)

*Primary Examiner* — Spencer E Bell
*Assistant Examiner* — Tinsae B Ayalew
(74) *Attorney, Agent, or Firm* — Leason Ellis LLP

(57) ABSTRACT

Integrated probes and probe systems suitable for attachment to a robotic arm of a remotely operated vehicle are disclosed. The probes and probe systems serve to perform cleaning operations and both cathodic protection (CP) voltage measurements and ultrasonic testing (UT) thickness measurements at an underwater surface. The cathodic protection measurement system includes one or more electrically conductive legs that extend outwardly from the probe. These legs are arranged about a cleaning tool and an ultrasonic sensor. When the integrated probe contacts the underwater surface, at least one leg contacts the surface, thereby providing a desired distance between the probe and the underwater surface for efficient cleaning and UT inspection. The underwater surface can be cleaned and CP and UT measurements can all be performed using a single, integrated probed during a single operation, without having to reposition the probe.

14 Claims, 2 Drawing Sheets

Figure 1:
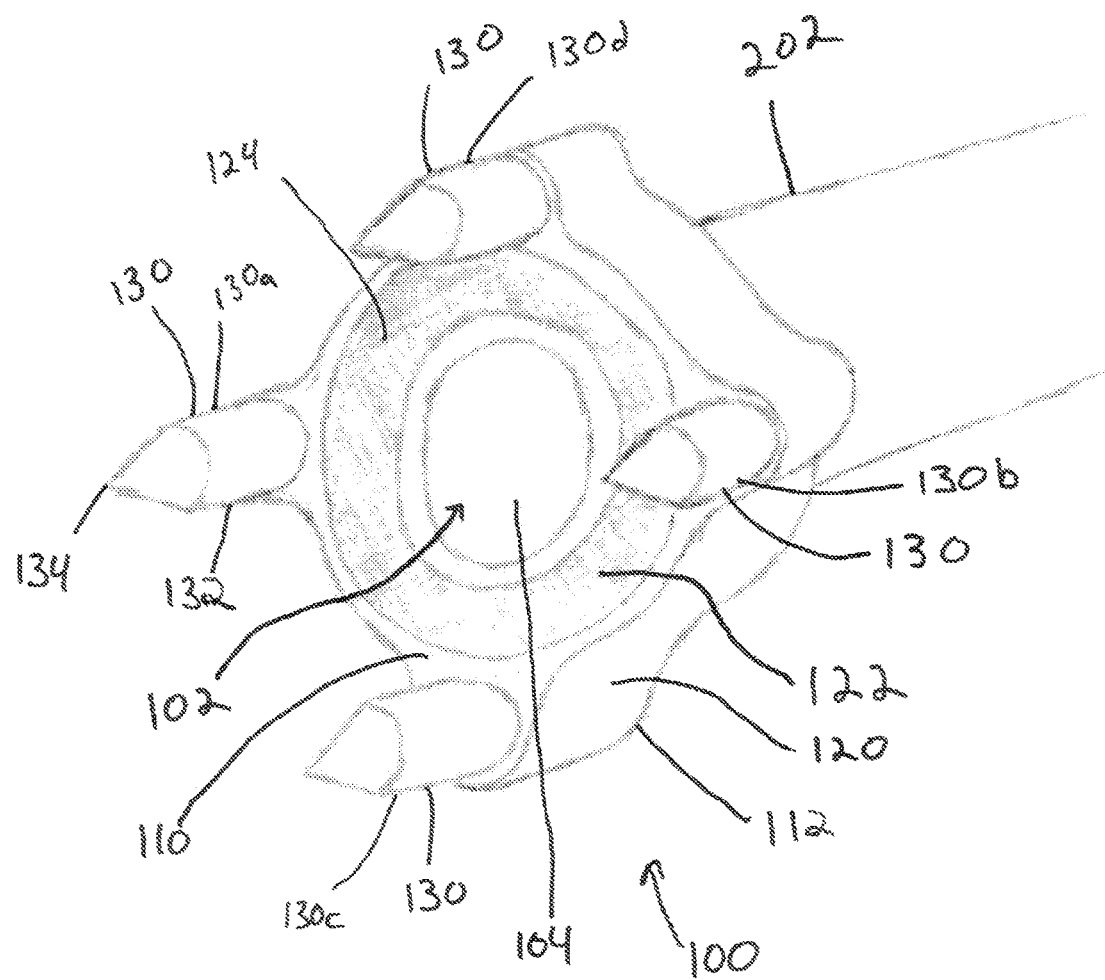

(51) Int. Cl.
| | |
|---|---|
| *G01B 17/02* | (2006.01) |
| *G01R 19/00* | (2006.01) |
| *B08B 9/023* | (2006.01) |
| *B08B 13/00* | (2006.01) |
| *B63B 59/08* | (2006.01) |
| *C23F 13/22* | (2006.01) |
| *G01N 29/22* | (2006.01) |
| *G01N 29/265* | (2006.01) |
| *G01N 17/02* | (2006.01) |
| *E02B 17/00* | (2006.01) |
| *B63G 8/00* | (2006.01) |

(52) U.S. Cl.
CPC ............. *B63B 59/08* (2013.01); *C23F 13/22* (2013.01); *G01B 17/02* (2013.01); *G01N 17/02* (2013.01); *G01N 29/225* (2013.01); *G01N 29/265* (2013.01); *G01R 19/0084* (2013.01); *B08B 2203/027* (2013.01); *B08B 2203/0217* (2013.01); *B63G 8/001* (2013.01); *B63G 2008/005* (2013.01); *C23F 2213/31* (2013.01); *E02B 17/0034* (2013.01); *G01N 2291/02854* (2013.01)

(58) Field of Classification Search
CPC ........... B08B 3/02; B08B 9/023; B08B 13/00; B08B 2203/0217; B08B 2203/027; B63B 59/08; C23F 2213/31; C23F 13/22; G01B 17/02; G01R 19/0084; B63G 8/001; B63G 2008/005; E02B 17/0034
USPC ......................................................... 134/198
See application file for complete search history.

(56) References Cited

U.S. PATENT DOCUMENTS

| | | | |
|---|---|---|---|
| 4,168,562 A | 9/1979 | Maasberg | |
| 4,444,146 A | 4/1984 | De Witz et al. | |
| 4,669,915 A | 6/1987 | Shatto, Jr. | |
| 4,674,915 A | 6/1987 | Shatto, Jr. | |
| 4,716,849 A | 1/1988 | Conn et al. | |
| 4,809,383 A | 3/1989 | Urakami | |
| 4,821,665 A | 4/1989 | Matthias et al. | |
| 4,890,567 A | 1/1990 | Caduff | |
| 5,205,174 A | 4/1993 | Silverman et al. | |
| 5,628,271 A | 5/1997 | McGuire | |
| 5,947,051 A | 9/1999 | Geiger | |
| 6,413,323 B2 | 7/2002 | Shook et al. | |
| 6,854,412 B1 | 2/2005 | Courson et al. | |
| 7,155,307 B2 | 12/2006 | Seemann | |
| 8,794,251 B2 | 8/2014 | Tor Mikal Ostervold et al. | |
| 9,061,736 B2 | 6/2015 | Smith | |
| 9,193,068 B2 | 11/2015 | Chin et al. | |
| 2011/0100400 A1 | 5/2011 | Tor Mikal Ostervold | |
| 2014/0081504 A1 | 3/2014 | Smith et al. | |
| 2014/0230713 A1 | 8/2014 | Kimura et al. | |
| 2016/0001857 A1 | 1/2016 | Ledda | |
| 2016/0264223 A1 | 9/2016 | Ferguson | |
| 2017/0057605 A1 | 3/2017 | Glenn et al. | |
| 2018/0073975 A1* | 3/2018 | Abdellatif | C23F 13/04 |

OTHER PUBLICATIONS

Souto, A. et. al., "Lappa: A new type of robot for underwater non-magnetic and complex hull cleaning." 6 pages.
Hobot V2 Multi-Surface Cleaning Robot—Robot Shop. Retrieved from http://www.robotshop.com/en/hobot-v2-multi-surface-cleaning-robot.html on Jan. 19, 2017. 5 pages.
Innospection. Advanced inspection solutions. Flexible Riser Inspection. Retriced from http://www.innospection.com/services/FlexibleRisers/ on Jul. 5, 2017. Copyright 2016.
4subsea. Repair Clamps Epic. Retrieved from https://www.4subsea.com/solutions/flexible-risers/epic/ on Jul. 5, 2017.

* cited by examiner

UNDERWATER VEHICLES WITH INTEGRATED SURFACE CLEANING AND INSPECTION

FIELD OF THE INVENTION

This patent application generally relates to cleaning, testing, measuring mechanisms, and more particularly to probe systems for cleaning and for ultrasonically measuring thickness and performing cathodic protection voltage readings in an underwater environment.

BACKGROUND OF THE INVENTION

Performing cleaning and inspection of underwater surfaces is often a difficulty and time consuming process that can require multiple, separate robotic vehicles and/or robotic vehicles including multiple, separate robotic arms and probes. Typically, a cleaning tool is first brought into contact with an underwater surface to be inspected to clean the surface so that inspection can be performed on the surface. Then the cleaning tool must be moved away from the surface that has been cleaning and a separate robot/probe must locate and be brought into contact with the area that was just cleaned to perform an inspection process. If multiple, types of inspections are required, separate robots/probes must be brought into contact with the cleaning area. Removing and repositioning separate probes/robots is can be time consuming, difficult, and expensive.

While some inspection robots include cleaning and inspection tools, they are typically located at different location along the vehicle. Accordingly, the vehicle must first clean an area of the surface and then move with respect to the surface to bring the sensor into position with respect to the area. This requires controlled movement of the robot to ensure proper alignment and also delays the process because the robot must move in between the cleaning and inspecting operations. Moreover, these systems typically require separate structures that provide a standoff between the robot and the surface. These separate structures increase the complexity, weight, and cost of the system.

The present invention offers a solution to one or more of these and other problems.

SUMMARY OF THE INVENTION

In one aspect of the invention, an integrated probe suitable for performing cleaning, cathodic protection voltage readings, and ultrasonic testing thickness measurements at an underwater surface substantially simultaneously is provided. The integrated probe includes a housing having a front surface and a rear surface. A cleaning jet tool having an orifice extends through the front surface of the housing. An ultrasonic probe is disposed within the housing. The ultrasonic probe has a transducer crystal and a flexible membrane arranged about the transducer crystal, and a couplant disposed within a gap between the flexible membrane and the transducer crystal. The integrated probe includes a cathodic inspection tool having one or more legs, each having an electrically conductive tip and a subsea housing containing a reference electrode, and each leg extending longitudinally away from the housing and arranged about the cleaning jet tool and ultrasonic probe. The one or more legs are passively adjustable in response to a force imparted when the one or more legs contact the underwater surface. The one or more legs extend away from the housing at a distance such that in a condition in which the conductive tip of the one or more legs is in contact with the underwater surface, the cleaning jet tool and ultrasonic probe are at a distance for effective cleaning and ultrasonic measuring, respectively.

According to a further aspect, the orifice of the cleaning jet tool is located at a central location of the housing.

According to another aspect, the ultrasonic probe extends about the orifice of the cleaning jet tool.

According to a still further aspect, the one or more legs provide a degree of flexibility that flexes to orient the cleaning jet tool and ultrasonic probe toward the underwater surface to be cleaning and inspected in a condition in which the one or more legs are in contact with the underwater surface.

According to a further aspect, the electrically conductive tip is made of stainless steel.

According to another aspect, the one or more legs are arranged about the ultrasonic probe as two pairs of diametrically opposed legs.

According to a further aspect, the at least one degree of freedom is provided by one or more joints coupling the housing to an external carrier.

According to another aspect, a system for performing cleaning, cathodic protection voltage readings, and ultrasonic testing thickness measurements at an underwater surface substantially simultaneously is provided. The system includes a remotely operated underwater vehicle having a robotic support arm with a distal end. An integrated probe for cleaning, measuring cathodic protection voltage, and ultrasonic testing thickness measurement coupled to the distal end of the robotic support arm is provided. The integrated provide includes a housing having a front surface and a rear surface. A cleaning jet tool having an orifice extending through the front surface of the housing. An ultrasonic probe is disposed within the housing, the ultrasonic probe having a transducer crystal and a flexible membrane arranged about the transducer crystal, and a couplant disposed within a gap between the flexible membrane and the transducer crystal. A cathodic inspection tool having one or more legs is provided. Each leg has an electrically conductive tip and a subsea housing containing a reference electrode, and each leg extending longitudinally away from the housing and arranged about the cleaning jet tool and ultrasonic probe. The one or more legs are passively adjustable in response to a force imparted when the one or more legs contact the underwater surface. The one or more legs extend away from the housing at a distance such that in a condition in which the conductive tip of the one or more legs is in contact with the underwater surface, the cleaning jet tool and ultrasonic probe are at a distance for effective cleaning and ultrasonic measuring, respectively.

According to a further aspect, the orifice of the cleaning jet tool is located at a central location of the housing.

According to a still further aspect, the ultrasonic probe extends about the orifice of the cleaning jet tool.

According to another aspect, the one or more legs provide a degree of flexibility that flexes to orient the cleaning jet tool and ultrasonic probe toward the underwater surface to be cleaning and inspected in a condition in which the one or more legs are in contact with the underwater surface.

According to a yet further aspect, the electrically conductive tip is made of stainless steel.

According to a still further aspect, the one or more legs are arranged about the ultrasonic probe as two pairs of diametrically opposed legs.

According to a further aspect, the at least one degree of freedom is provided by one or more joints coupling the housing to an external carrier.

According to another aspect, a method of performing a cleaning operation, cathodic protection voltage readings and ultrasonic testing thickness measurements on an underwater surface with an integrated probe having a cleaning jet tool, an ultrasonic probe, and at least one leg with an electrically conductive tip is provided. The method includes the steps of positioning a remotely operated vehicle, having at least one robotic arm with the integrated probe disposed at a free end of the robotic arm and the integrated probe coupled to the arm end effector, in proximity to the underwater surface. The underwater surface is contacted with the integrated probe such that the at least one leg with an electrically conductive tip contacts the underwater surface, wherein a length of the at least one leg positions the cleaning jet tool and ultrasonic probe at a desired distance from the underwater surface for effective cleaning and measurement. The underwater surface is cleaned by causing a high pressure fluid to exit the cleaning jet tool and impact the underwater surface. The method includes the steps of measuring, by the at least one leg, a voltage at the underwater surface and measuring, by the ultrasonic probe, a thickness of the underwater surface.

According to a further aspect, the steps of cleaning, measuring a voltage, and measure a thickness are all performed without repositioning the remotely operated vehicle.

According to a still further aspect, the steps of cleaning, measuring a voltage, and measure a thickness are all performed during a single contacting step.

BRIEF DESCRIPTION OF THE DRAWING FIGURES

The accompanying drawing figures illustrate exemplary embodiments and are not intended to be limiting of the invention. Among the drawing figures, like references are intended to refer to like or corresponding parts.

Figure 2:
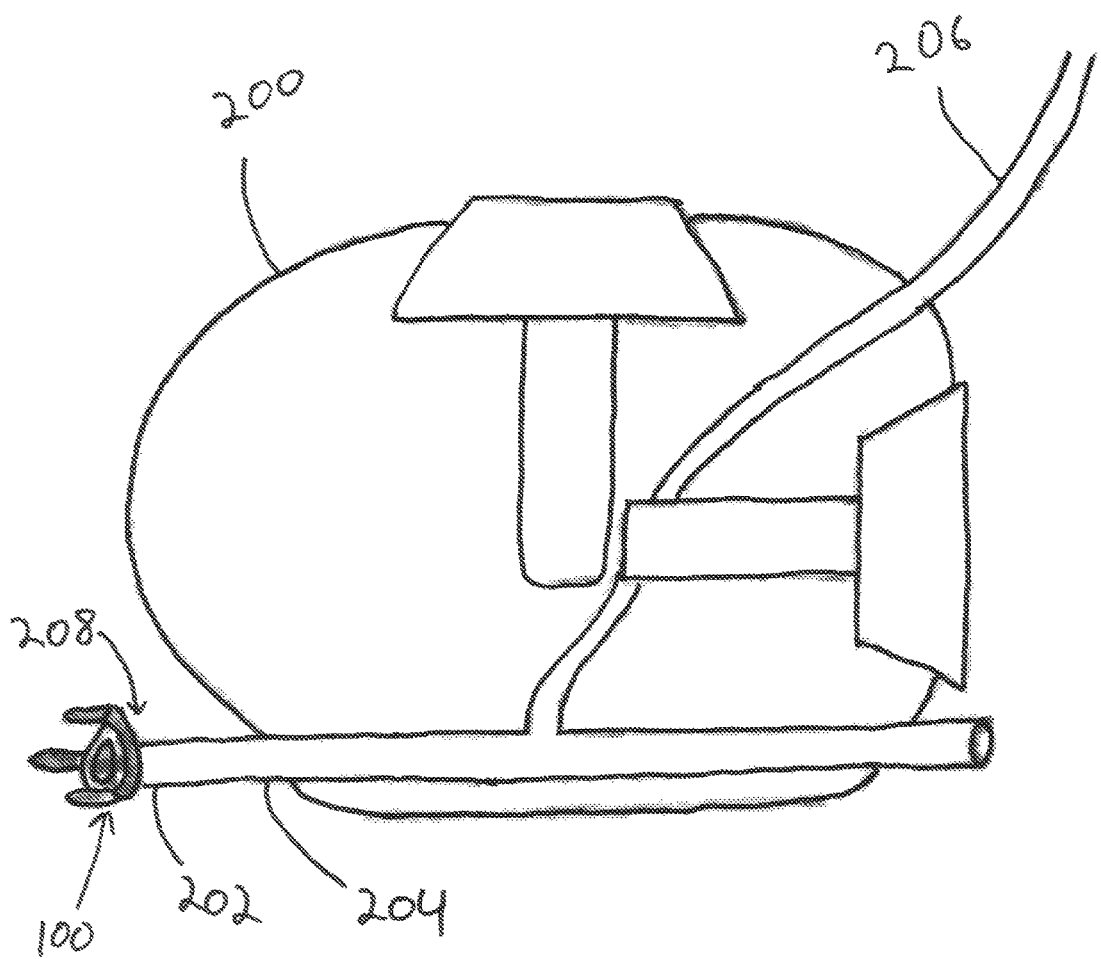

FIG. 1 illustrates an isometric view of an integrated cleaning, CP and UT probe system in accordance with at least one embodiment of the present application; and FIG. 2 illustrates a side view of the integrated cleaning, CP and UT probe system of FIG. 1 mounted on an underwater robotic vehicle.

DETAILED DESCRIPTION OF CERTAIN EMBODIMENTS OF THE INVENTION

The invention is now described with reference to the accompanying drawings, which form a part hereof, and which show, by way of illustration, example implementations and/or embodiments of the present invention. It is to be understood that other embodiments can be implemented and structural changes can be made without departing from the spirit of the present invention. Among other things, for example, the disclosed subject matter can be embodied as methods, devices, components, or systems.

Furthermore, it is recognized that terms may have nuanced meanings that are suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter can be based upon combinations of individual example embodiments, or combinations of parts of individual example embodiments.

In accordance with the present application, embodiments are provided that are directed to integrated probes and integrated probe systems for inspecting and cleaning. The integrated probe can include a cleaning tool and can further include sensors for measuring cathodic protection (CP) voltage and measuring surface thickness using ultrasonic testing (UT) in which the delay between performing a cleaning operation and taking each measurement is minimized. In this way, cleaning operations and CP and UT measurements can be performed either in quick succession or substantially simultaneously. For example, a cleaning operation and both CP and UT measurements can be performed during a single touchdown at a specific underwater surface (or an "inspection surface"), such as an underwater pipeline or piling, or the underside of a moored ship hull.

In one aspect, as shown in FIG. 2, the integrated probes 100 as provided in one or more embodiments herein can be coupled to a single robotic arm of a remotely operated vehicle (ROV) 200 at, for example, the free end 202 of a robotic arm 204. For example, a rear surface 112 of the probe housing 120 can be connected to the robotic arm 204 via a flexible joint 208 (e.g., ball and socket, linkage, etc.) that provides at least one degree of freedom of movement of the integrated probe 100. The structural limitations of typical ROVs restrict their robotic arms to only a single interchangeable or permanently mounted probe per robotic arm, and such arms lack the dexterity necessary to perform a cleaning operation and simultaneous CP and UT measurements. Thus, conventionally, in order for a ROV to perform a cleaning operation and both CP and UT measurements in a single trip, it must have at least three robotic arms and/or complex structures. Each robotic arm is heavy, and only large, work-class ROVs can include three or more robotic arms. In some cases, conventional measurement methods require a complete probe exchange (e.g., from CP to UT, or vice versa) at the arm to perform the second measurement. Such limited actuation capabilities result in inherent delay (and thus increased costs due to necessarily increased ROV time) because the two probe measurement systems must switch between two wholly separate CP and UT probes, and must reorient the second probe to the same inspection surface where the first probe measurement was taken. This process is further complicated when also incorporating a cleaning operation because in addition to changing probes, it is necessary to realign the measurement probes to measure the area of the structure that was cleaned. The present application does not require the implementation of two separate CP and UT probes and a further separate cleaning tool. Rather, cleaning, CP inspection, and UT inspection can be accomplished using a single probe at a location without having to reposition multiple probes/tools to perform these operations.

Further, the integrated probe systems herein provide the advantage of being implementable by small, lightweight class ROVs having only a single robotic arm, such as electric ROVs, general class ROVs, inspection class ROVs, and observation class ROVs. Smaller class ROVs can be necessary if the inspection surface has accessibility issues (e.g., shallow water sites), or if there are power supply limitations.

In one or more embodiments, the integrated probe system 100 includes a central water jet cleaning tool 102, a centrally located, ring-shaped UT sensor or transducer 122 (e.g., a piezo-ceramic crystal) surrounding the cleaning tool, and a further surrounding array of electrically conductive legs 130 having tips or fixtures that are articulated and passively adjustable for performing CP measurements. The electrically conductive legs are not rigid, but rather have some flexibility with respect to how they contact an underwater surface. In this way, when the electrically conductive legs contact an underwater surface, they passively adjust to orient the cleaning tool and UT sensor transverse to the inspection surface. At the same time, the legs conduct the cathodic protection electrical voltage associated with the surface, such as with electrically conductive steel tips, thereby acting as a CP probe. Accordingly, the legs of the CP probe provide multiple functions in that they provide contact points for performing CP measurement and further function position the cleaning tool relative to the inspection surface such that the cleaning tool is in the proper orientation and distance with respect to the inspection surface for effective cleaning. In this way, cleaning and CP and UT measurements can be conducted substantially simultaneously, thereby reducing time for cleaning and measurement inspection time, the size and weight added to the robotic arm, and improving ROV agility.

A sensor housing 110 is located at a distal end of robotic arm 120. An ultrasonic ring-shaped probe 122 is contained within the sensor housing 110 and arranged below an outer flexible membrane 124. In one or more embodiments, the ultrasonic probe 122 can comprise a plurality of piezoceramic crystals arranged in a ring shape. The ultrasonic probe 122 can be selected to emit and receive ultrasonic waves at a variety of particular frequencies. For example, the ultrasonic sensor can operate at frequencies of 2.0 MHz, 2.25 MHz, 3.5 MHz, 5.0 MHz, or 7.5 MHz. To facilitate ultrasonic transmission, a film of membrane couplant is located, for example, within a gap between the ultrasonic probe 122 and the flexible membrane 124 of the sensor housing 110. Membrane couplant can comprise a viscous liquid, gel, or paste used to minimize the amount of air in the gap between the sensor and the membrane. For example, the membrane couplant can be propylene glycol, glycerin, silicone oil, or various commercially available gels.

The CP probe functionality of the integrated probe system 100 is provided by measuring the voltage difference between one or more reference electrodes (or "reference cells") and one or more voltage electrodes that contact the inspection surface. The reference electrode is kept electrically insulated from the voltage electrode and is typically submerged in water (such as the underwater environment itself). In one or more embodiments, CP probe functionality of the integrated probe system 100 is provided by one or more electrically conductive legs 130 that extend longitudinally beyond the front surface of the housing 110. The legs 130 can be integrally formed with the housing 110 or can be separate cathodic probes that are installed at the housing. In either case, the legs can be articulated—i.e., connected to allow flexibility of movement. In one or more embodiments, the legs 130 can include a housing 132 that contains one or more reference cells within that serves as a reference electrode, and a conductive tip 134 at the end of the housing that serves as a voltage electrode. The conductive tip 134 is made of conductive metals, such as steel or other alloys that can conduct voltage at the underwater surface to be measured. The reference cell housed in the subsea housing 132 must be exposed to water and can be of the type used in conventional cathodic protection potential probe construction, such as a silver/silver chloride half-cell or a pure zinc electrode. In other embodiments, the reference electrode is located at the outer surface of, or housed within, a ROV or its robotic arm. The electrically conductive legs 130 are in electrical connection with a voltage processing device, such as a voltmeter (not shown), which can be located at the integrated probe system 100, an ROV or surface-side in order to record and/or display voltage readings taken at a measurement site. In embodiments implementing an ROV, the ROV can have an umbilical cable leading to an above-surface location to couple, by an electrical cable, a voltmeter to the non-tip end of the legs 130, such that when the conductive tip 134 contacts the underwater surface (e.g., a pipeline), the potential is measured by the voltmeter. At least one voltage electrode at one of the tips 134 of legs 130 must be in contact with the inspection surface to obtain an accurate cathodic potential reading, but it is not necessary that each leg 130 be in contact with the inspection surface when the reading is made. The present application does not suffer from inaccurate readings due to various resistive paths presented by each leg 130 during voltage reading.

In one or more embodiments, the tips 134 of legs 130 are shaped as cones having circular or elliptical bases. In other embodiments, the tips 134 of legs 130 are pyramid shaped, rectangular prisms, semicircular, pointed, flat, or have rounded ends. In this way, the tips 134 are re-configurable or interchangeable to achieve various contact configurations. For example, the tips 134 can be mobile metallic rollers, wheeled tips or ball casters instead of static stainless steel tips. Such a configuration will reduce impact on a ROV arm end effector upon touchdown at an inspection surface (e.g., a steel surface of a pipe) and allow for translational motion across the inspection surface when performing scans instead of spot checks.

The cleaning functionality of the integrated probe system 100 is provided by fluid jet cleaning tool 102. The jet cleaning tool 102 includes a central orifice 104 that directs high pressure fluid toward the surface to be inspected. The high-pressure fluid can be fresh water, sea water, cleaning fluid, or a combination of fluid with suspended cleaning particles. The fluid exits the central orifice 104 at a high pressure and impact the surface to be inspected. The high pressure nature of the fluid works to blast away debris located on the surface, such as marine growth and or sediment. The high pressure fluid can be supplied by an umbilical tether 206 in which the high pressure fluid is provided from a surface support system. Alternatively, the robot 200 can include a fluid reservoir and pump system that can supply the high pressure fluid. As another alternative, the robot can include a pump that can intake surrounding sea water and direct it at high pressure through the jet cleaning tool 102.

During operation of integrated probe system 100, in order to perform cleaning and both CP and UT measurements substantially simultaneously, the clean, CP and UT aspects of the integrated probe system need to be brought into proximity to the inspection surface. Sufficient proximity is dependent upon the effectiveness of the jet cleaning tool 102 and/or the calibration of the ultrasonic probe 122, meaning that the cleaning tool has a certain cleaning effectiveness range and the ultrasonic probe has a certain effective measurement range as a result of the properties of water in between the probe and the surface, the materials of the surface, and other considerations. For example, the effective measurement range of the ultrasonic probe 122 means that it needs to abut or be within a few millimeters of the inspection surface to perform a successful measurement. If the ultrasonic probe 122 is any further from the inspection surface, it will lose signal integrity and fail to acquire a reading. In one or more embodiments, the ultrasonic probe 122 has an effective measurement range of 0-2 mm. The further that the ultrasonic probe 122 is from the inspection surface, the less accurate that the UT measurement is. The cleaning jet tool can be adjusted to accommodate the effectiveness range of the UT probe. For example, the diameter and/or shape of the orifice can be adjusted so that the pressure of the fluid exiting the orifice or the pressure of the fluid being supplied to the tool can be adjusted. By changing the nozzle shape and/or fluid supply pressure, the cleaning tool can be effective to clean the surface at the same distance that the UT probe can perform measurements. In this way, cleaning and UT inspection can be performed without having to reposition the probe between cleaning and UT inspection operations.

In one or more embodiments, the electrically conductive legs 130 must contact the inspection surface in order to take a CP voltage measurement. As such, integrated probe system 100 can be arranged such that the legs 130 contact the inspection surface while both the cleaning jet tool 102 and the ultrasonic probe 122 are positioned within their effectiveness ranges for cleaning and measurement (e.g., 0-2 mm from the inspection surface). The arrangement of legs 130 with regard to the cleaning jet tool 102 and ultrasonic probe 122 within the sensor housing 120 can be configured to accommodate the diameter or curvature of particular inspection surfaces. For example, in one or more embodiments, the legs 130 extend a distance beyond the sensor housing 120. In this way, when the integrated probe system 100 is brought in proximity to the inspection surface, one or more of the legs 130 will contact the surface, but the cleaning jet tool and ultrasonic probe 122 will not, though the cleaning jet tool and ultrasonic probe will still be close enough to the surface to be within its effective range for performing cleaning and accurate UT measurements. In one or more embodiments, the legs 130 extend 0.5 mm, 1 mm, 1.5 mm, 2 mm, or 2.5 mm beyond the sensor housing 120. In other embodiments, the legs 130 are aligned with the sensor housing 120. Longer legs 130 can be implemented for inspection surfaces having smaller diameters (e.g., approximately 10 cm or less) because for smaller inspection surfaces, the front surface width of the integrated probe system 100 is comparable to the inspection surface and thus not all the legs can contact the surface at once, though if at least one leg contacts the surface and the other legs are oriented to surround the surface, then cleaning jet tool and the ultrasonic probe 122 will be oriented at the inspection surface within its effective measurement range. Accordingly, the legs 130 of the CP probe provides multiple function in that the provide contact points necessary for performing a CP measurement and further orient and set the distance between the cleaning jet tool and the surface for effective cleaning and also orient and set the distance between the UT probe and the surface for effective measurements. In this way, the integrated probe system 100 provides an efficient and compact design that permits for cleaning, and both UT and CP measurements all during a single landing of the probe, nearly simultaneously, without have to reposition or use multiple, separate probes.

The decision of whether and how much the legs 130 extend beyond the sensor housing 120 and where to arrange the legs at the front surface of the integrated probe system 100 can be dependent upon the particular arrangement desired. For example, the legs 130 can be advantageously arranged around a sensor housing 120 located in the center of the front surface 110 of the housing 120, such that each leg 130 is equidistant from both one another and the sensor housing. Centrally locating the sensor housing 120 in this way maximizes the likelihood that a UT thickness measurement is performed as one or more of the legs 130 contacts an inspection surface. The distance that the legs 130 are from the sensor housing 120 can be varied, depending on the arrangement desired to inspect a particular surface. For example, an arrangement in which the legs 130 are near to the sensor housing 120 decreases any differences in measurement lag between taking a CP voltage and UT thickness measurement and increases the precision of the spot inspection and the effectiveness of the spot cleaning, whereas spacing the legs 130 relatively further from the sensor housing provides a wider cleaning and inspection area and can provide an alignment assist (i.e., one leg contacts the surface and the leg flexes and/or the housing 120 shifts in response to that force, thereby pushing one or more other legs into contact as well).

In a particular embodiment illustrated by FIGS. 1 and 2, four articulated electrically conductive legs 130 are arranged around an ultrasonic probe 122. FIG. 1 illustrates a first pair of legs 130a, 130b that are diametrically opposed to one another. A second pair of legs 130c, 130d is also diametrically opposed to one another. In this embodiment, the four legs 130a-130d are equally spaced 90 degrees apart about the ultrasonic probe 122. This arrangement provides maximum range for at least one leg to be able to contact the inspection surface in order to obtain a voltage reading. However, depending on the particular application, other electrically conductive leg arrangements of four legs can be contemplated in which the legs are not equally spaced apart.

Furthermore, the flexibility of legs 130 in conjunction with the flexibility of inner gimbal 110 causes the ultrasonic probe 122 to be aligned on the inspection surface within a certain margin (e.g., the front surface of housing 110 is substantially transversely perpendicular to the target surface). This passive alignment of the ultrasonic probe 122 by the electrically conductive legs 130 allows for cleaning and simultaneous CP voltage and UT measurements to be performed without having to reposition the probe, or at least in a single probing of the inspection surface, or without having to use different probes to provide differing functions. In one or more embodiments, a proximity sensor is coupled with the ultrasonic probe 122 to aid in positioning at the inspection surface. For example, the proximity sensor can be an infrared or acoustic sensor located inside sensor housing 120 at or adjacent to the flexible membrane of ultrasonic probe 122.

Notably, the figures and examples above are not meant to limit the scope of the present application to a single implementation, as other implementations are possible by way of interchange of some or all of the described or illustrated elements. For example, the integrated probe system can be mounted on an articulated coupling mechanism that can provide additional degrees of freedom for the probe to contact the surface, as is disclosed in U.S. Provisional Application Ser. No. 62/395,162, filed Sep. 15, 2016, which is hereby incorporated by reference in its entirety. Moreover, where certain elements of the present application can be partially or fully implemented using known components, only those portions of such known components that are necessary for an understanding of the present application are described, and detailed descriptions of other portions of such known components are omitted so as not to obscure the application. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present application encompasses present and future known equivalents to the known components referred to herein by way of illustration.

The foregoing description of the specific implementations will so fully reveal the general nature of the application that others can, by applying knowledge within the skill of the relevant art(s) (including the contents of the documents cited and incorporated by reference herein), readily modify and/or adapt for various applications such specific implementations, without undue experimentation, without departing from the general concept of the present application. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various implementations of the present application have been described above, it should be understood that they have been presented by way of example, and not limitation. It would be apparent to one skilled in the relevant art(s) that various changes in form and detail could be made therein without departing from the spirit and scope of the application. Thus, the present application should not be limited by any of the above-described example implementations.

What is claimed:

1. An integrated probe suitable for performing cleaning, cathodic protection voltage readings, and ultrasonic testing thickness measurements at an underwater surface, comprising:
   a housing having a front surface and a rear surface;
   a cleaning jet tool having an orifice extending through the front surface of the housing;
   an ultrasonic probe disposed within the housing, the ultrasonic probe having a transducer crystal and a flexible membrane arranged about the transducer crystal; and
   a cathodic inspection tool having one or more legs, each having an electrically conductive tip and a subsea housing containing a reference electrode, each leg extending longitudinally away from the housing and arranged about the cleaning jet tool and ultrasonic probe,
   wherein the one or more legs are passively adjustable in response to a force imparted when the one or more legs contact the underwater surface, and
   wherein the one or more legs extend away from the housing at a distance such that in a condition in which the conductive tip of the one or more legs is in contact with the underwater surface, the cleaning jet tool and ultrasonic probe are at a distance for effective cleaning and ultrasonic measuring, respectively.

2. The integrated probe according to claim 1, wherein the orifice of the cleaning jet tool is located at a central location of the housing.

3. The integrated probe according to claim 1, wherein the ultrasonic probe extends about the orifice of the cleaning jet tool.

4. The integrated probe of claim 1, wherein the one or more legs provide a degree of flexibility that flexes to orient the cleaning jet tool and ultrasonic probe toward the underwater surface to be cleaning and inspected in a condition in which the one or more legs are in contact with the underwater surface.

5. The integrated probe according to claim 1, wherein the electrically conductive tip is made of stainless steel.

6. The integrated probe according to claim 1, wherein the one or more legs are arranged about the ultrasonic probe as two pairs of diametrically opposed legs.

7. The integrated probe according to claim 1, further comprising one or more joints coupling the housing to an external carrier.

8. A system for performing cleaning, cathodic protection voltage readings, and ultrasonic testing thickness measurements at an underwater surface, comprising:
   a remotely operated underwater vehicle having a robotic support arm with a distal end;
   an integrated probe for cleaning, measuring cathodic protection voltage, and ultrasonic testing thickness measurement coupled to the distal end of the robotic support arm, wherein the integrated probe includes:
   a housing having a front surface and a rear surface;
   a cleaning jet tool having an orifice extending through the front surface of the housing;
   an ultrasonic probe disposed within the housing, the ultrasonic probe having a transducer crystal and a flexible membrane arranged about the transducer crystal; and
   a cathodic inspection tool having one or more legs, each having an electrically conductive tip and a subsea housing containing a reference electrode, each leg extending longitudinally away from the housing and arranged about the cleaning jet tool and ultrasonic probe,
   wherein the one or more legs are passively adjustable in response to a force imparted when the one or more legs contact the underwater surface, and
   wherein the one or more legs extend away from the housing at a distance such that in a condition in which the conductive tip of the one or more legs is in contact with the underwater surface, the cleaning jet tool and ultrasonic probe are at a distance for effective cleaning and ultrasonic measuring, respectively.

9. The system according to claim 8, wherein the orifice of the cleaning jet tool is located at a central location of the housing.

10. The system according to claim 8, wherein the ultrasonic probe extends about the orifice of the cleaning jet tool.

11. The system of claim 8, wherein the one or more legs provide a degree of flexibility that flexes to orient the cleaning jet tool and ultrasonic probe toward the underwater surface to be cleaning and inspected in a condition in which the one or more legs are in contact with the underwater surface.

12. The system according to claim 8, wherein the electrically conductive tip is made of stainless steel.

13. The system according to claim 8, wherein the one or more legs are arranged about the ultrasonic probe as two pairs of diametrically opposed legs.

14. The system according to claim 8, further comprising one or more joints coupling the housing to an external carrier.

* * * * *